US012708634B2

(12) United States Patent
Panagiotakopoulos et al.

(10) Patent No.: US 12,708,634 B2
(45) Date of Patent: Aug. 18, 2026

(54) PSILOCYBIN DERIVED COMPOSITIONS AND METHODS USING SAME

(71) Applicant: 1242753 Ontario Inc., London (CA)

(72) Inventors: Natalia Panagiotakopoulos, Golden Beach, FL (US); Bill Panagiotakopoulos, Golden Beach, FL (US); Najla Guthrie, Ontario (CA); Andrew Charrette, Hollywood, FL (US)

(73) Assignee: 1242753 Ontario Inc., London (CA)

( * ) Notice: Subject to any disclaimer, the term of this patent is extended or adjusted under 35 U.S.C. 154(b) by 0 days.

(21) Appl. No.: 17/948,180

(22) Filed: Sep. 19, 2022

(65) Prior Publication Data

US 2023/0089848 A1 Mar. 23, 2023

Related U.S. Application Data

(60) Provisional application No. 63/245,451, filed on Sep. 17, 2021.

(51) Int. Cl.

| | |
|---|---|
| ***A61K 31/675*** | (2006.01) |
| ***A61K 31/05*** | (2006.01) |
| ***A61K 31/4045*** | (2006.01) |
| ***A61K 35/747*** | (2015.01) |

(52) U.S. Cl.

CPC ........ *A61K 31/675* (2013.01); *A61K 31/4045* (2013.01); *A61K 35/747* (2013.01)

(58) Field of Classification Search

None

See application file for complete search history.

(56) References Cited

U.S. PATENT DOCUMENTS

| | | | | |
|---|---|---|---|---|
| 2019/0105313 | A1* | 4/2019 | Stamets | A61K 36/07 |
| 2021/0251976 | A1 | 8/2021 | Stamets | |
| 2021/0268046 | A1 | 9/2021 | Salmons et al. | |
| 2021/0346346 | A1* | 11/2021 | Chadeayne | A61K 31/4045 |
| 2022/0280482 | A1 | 9/2022 | Barrow et al. | |
| 2022/0313713 | A1 | 10/2022 | Moss et al. | |
| 2022/0331344 | A1* | 10/2022 | Greenbaum | A61K 36/06 |

FOREIGN PATENT DOCUMENTS

| | | | | |
|---|---|---|---|---|
| WO | WO-2018/135943 | | 7/2018 | |
| WO | 2019/099745 | A1 | 5/2019 | |
| WO | WO-2021/074706 | | 4/2021 | |
| WO | WO-2021/101926 | | 5/2021 | |
| WO | WO-2021253123 | A1 * | 12/2021 | A61K 31/404 |
| WO | WO-2022272176 | A1 * | 12/2022 | |

OTHER PUBLICATIONS

MayoClinic. Rheumatoid arthritis. Retrieved from the Wayback Machine on Aug. 28, 2023, https://web.archive.org/web/20210817185819/https://www.mayoclinic.org/diseases-conditions/rheumatoid-arthritis/diagnosis-treatment/drc-20353653. Published Aug. 17, 2021. (Year: 2021).*

Rianjongdee, Serena. "Anti-inflammatory effects of omega-3 fatty acids could help reduce depression." EurekaAlert! Retrieved from the internet on Nov. 13, 2023, https://www.eurekalert.org/news-releases/467522, Published Jun. 15, 2021. (Year: 2021).*

OM Mushroom Superfood. Your Guide to Lion's Mane Mushroom Benefits and How to Use This Superfood. Retrieved from the Internet on Nov. 13, 2023, https://ommushrooms.com/blogs/blog/lions-mane-mushroom-benefits-m2. Published Jul. 1, 2021. (Year: 2021).*

Del Toro-Barbosa M, Hurtado-Romero A, Garcia-Amezquita LE, García-Cayuela T. Psychobiotics: Mechanisms of Action, Evaluation Methods and Effectiveness in Applications with Food Products. Nutrients. Dec. 19, 2020;12(12):3896. (Year: 2020).*

PubChem. 3-[2-(methylamino)ethyl]-1H-indol-4-ol Retrieved from the Internet on Dec. 19, 2020, https://pubchem.ncbi.nlm.nih.gov/compound/14107683. (Year: 2023).*

Repke et al. Baeocystin in Psilocybe similanceata. Jn of Pharmaceutical Sciences. vol. 66, Issue 1, Jan. 1977. (Year: 1977).*

Mushrooms of the National Forests in Alaska. USDA. Retrieved from the Internet on Jan. 29, 2025, https://www.fs.usda.gov/Internet/FSE_DOCUMENTS/stelprdb5414170.pdf. Published Feb. 2013. (Year: 2013).*

Psilocin, PubChem. Retrieved from the Internet on Jan. 29, 2025, https://pubchem.ncbi.nlm.nih.gov/compound/4980#section=Depositor-Supplied-Synonyms&fullscreen=true. (Year: 2025).*

Psilocybin, PubChem. Retrieved from the Internet on Jan. 29, 2025, https://pubchem.ncbi.nlm.nih.gov/compound/10624#section=Depositor-Supplied-Synonyms&fullscreen=true (Year: 2025).*

Baeocystin, PubChem. Retrieved from the Internet on Jan. 29, 2025, https://pubchem.ncbi.nlm.nih.gov/compound/161359#section=Depositor-Supplied-Synonyms&fullscreen=true (Year: 2025).*

Norpsilocin, PubChem. Retrieved from the Internet on Jan. 29, 2025, https://pubchem.ncbi.nlm.nih.gov/compound/14107683#section=Depositor-Supplied-Synonyms&fullscreen=true (Year: 2025).*

(Continued)

*Primary Examiner* — Lauren Wells

(74) *Attorney, Agent, or Firm* — Arnall Golden Gregory LLP

(57) ABSTRACT

Described herein are formulations for treating, preventing, or ameliorating one or more of irritable bowel syndrome (IBS), rheumatoid arthritis (RA), fibromyalgia, post-traumatic stress disorder, PTSD, neuropathic pain, or symptoms associated with any of the foregoing. The formulations disclosed herein comprise a therapeutic dose of one more of psilocybin, psilocin, baeocystin, and norpsilocin. The formulations disclosed herein may also comprise one or more cannabinoids, such as cannabidiol (CBD), one or more psychobiotic compounds, such as *Lactobacillus rhamnosus* JB-1, one or more prebiotics, such as sorbitol or alginate, *Hericium erinaceus* or extract thereof, brain derived neurotrophic factor (BDNF), and a docosahexaenoic acid (DHA)-rich oil. Also described herein are methods utilizing the aforementioned compositions.

11 Claims, 1 Drawing Sheet

(56) References Cited

OTHER PUBLICATIONS

Glatfelter et al. Structure-Activity Relationships for Psilocybin, Baeocystin, Aeruginascin, and Related Analogues to Produce Pharmacological Effects in Mice, ACS Pharmacology & Translational Science, published 2022 (Year: 2022).*

Elsayed et al., "Mushrooms: A Potential Natural Source of Anti-Inflammatory Compounds for Medical Applications," Hindawi Publishing Corporation, Mediators of Inflammation, 2014, [online]. Retrieved from the Internet: <URL: https://www.hindawi.com/journals/mi/2014/805841/>.

International Search Report and Written Opinion issued in PCT/US2022/044039, mailed Dec. 15, 2022.

Lin, "Case Report: Resolution of Rheumatoid Arthritis in a Patient Consuming Psilocybin; Mushrooms," Journal of healthcare, 2020; 3(1): pp. 25-32.

Milne et al., "Metabolic engineering of *Saccharomyces cerevisiae* for the de nova production of psilocybin and related tryptamine derivatives," Metabolic Engineering, 2020; 60: pp. 25-36.

NATOF9, Psilocybin helped heal my Irritable Bowel Disease, [online], Published Mar. 5, 2017, [retrieved on Apr. 26, 2023] Retrieved from the Internet: <URL: https://www.shroomery.org/forums/showflat.php/Number/24137933>.

Third Party Observations submitted in PCT/US2022/044039, submitted Apr. 26, 2023.

Berge et al., "Pharmaceutical Salts", Journal of Pharmaceutical Sciences, 1977; 66(1): pp. 1-19.

Carhart-Harris et al., "Psilocybin with psychological support for treatment-resistant depression: six-month follow-up," Psychopharmacology, 2018; 235, 399-408.

Griffiths et al., "Psilocybin produces substantial and sustained decreases in depression and anxiety in patients with life-threatening cancer: A randomized double-blind trial," J Psychopharmacol, 2016; 30(12): pp. 1181-1197.

Grob et al., "Pilot study of psilocybin treatment for anxiety in patients with advanced-stage cancer," Arch Gen Psychiatry, 2011; 68(1): pp. 71-78.

Phan et al., "Edible and Medicinal Mushrooms: Emerging Brain Food for the Mitigation of Neurodegenerative Diseases," J. Med. Food, 2017; 20(1): pp. 1-10.

European Search Report (Supplementary), issued in related Application No. EP 22870838.4, mailed Jun. 18, 2025.

Flanagan et al., "Psychedelics as anti-inflammatory agents," Int Rev Psychiatry, 2018; 30(4): pp. 363-375.

UK Examination Report, issued in related Application No. GB 2404882.9, mailed Feb. 18, 2025.

Whelan et al., "Lysergic acid diethylamide and psilocybin for the management of patients with persistent pain: a potential role?" Pain Management, Future Medicine, 2018; 8(3): pp. 217-229.

* cited by examiner

Screening Assessments

-6 to -1 week

Baseline Assessments

Combination Microdose Product

Combination Microdose Product + Trauma-focused psychotherapy

Placebo

Placebo + Trauma-focused psychotherapy

Weekly Phone Calls 8 week Treatment Period

Week 9 Assessments

Week 13 Assessments

Week 21 Assessments

PSILOCYBIN DERIVED COMPOSITIONS AND METHODS USING SAME

CROSS-REFERENCE TO RELATED APPLICATIONS

This application claims priority to U.S. Provisional Application No. 63/245,451 filed on Sep. 17, 2021, the disclosure of which is incorporated herein by reference in its entirety.

BACKGROUND

Recently, there has been scientific interest in using psilocybin as a therapeutic. In some instances, psilocybin has demonstrated positive clinical results in treating psychiatric conditions. For example, Grob et al. have demonstrated an oral dose (0.2 mg/kg) of psilocybin decreased depression [Beck Depression Inventory (BDI)] and anxiety [State-Trait Anxiety Inventory (STAI)] more than placebo in the 2 weeks following each of the two conditions in patients with advanced-stage cancer and caused no clinically significant adverse events. Similarly, Griffiths et al. compared the efficacy of two oral psilocybin doses (0.31-0.43 mg/kg or 0.14-0.043 mg/kg) administered to patients diagnosed with one of multiple possible DSM-IV mood- or anxiety-related disorders in relation to a life-threatening cancer diagnosis and demonstrated large and persisting reductions in BDI and STAI scales at a six-month follow-up following treatment. Outside of cancer diagnoses, psilocybin has also demonstrated clinical significance in treatment-resistant major depression. Carhart-Harris et al. demonstrated that patients receiving two oral psilocybin doses (10 mg followed by 25 mg a week later) showed significantly decreased depressive symptoms (BDI) at 1 week and 3 months post-treatment. Similar results were seen for anxiety symptoms (STAI), and psilocybin showed no clinically significant adverse events.

The 5-hydroxytryptamine type 2A (5-$HT_{2A}$) receptor is a G protein-coupled receptor of serotonin for which psilocybin, and other psychedelic compounds, have been documented to activate thereby eliciting a response in the central nervous system that is associated with psychedelic compounds, i.e., neuronal excitation, hallucinations, out-of-body-experiences, and fear. Although some research has into depression and similar disorders, needs exist for the identification of psilocybin for other therapeutic and nutraceutical uses. The inventors have identified other conditions associated with the 5-$HT_{2A}$ receptor, such as rheumatoid arthritis (RA), fibromyalgia, and irritable bowel syndrome (IBS), which are associated with polymorphisms and/or mutations in the gene encoding for the 5-$HT_{2A}$ receptor, and hypothesize that activation of the 5-$HT_{2A}$ receptor may provide treatment, amelioration, and/or prevention of these conditions and/or symptoms associated therewith.

In light of these findings, the inventors have identified a growing demand to develop and evaluate compounds that activate the 5-$HT_{2A}$ receptor. The inventors have noted the relationship between the 5-$HT_{2A}$ receptor and conditions such as rheumatoid arthritis (RA), irritable bowel syndrome (IBS), and fibromyalgia, and that compounds that activate the 5-$HT_{2A}$ receptor can alleviate, ameliorate, cure, treat, or prevent these ailments have demonstrated therapeutic promise. The inventors have identified that psilocybin and other 5-$HT_{2A}$ receptor agonists, alone or in combination with each other and/or other compounds, are believed to confer many potential benefits to subjects to address such conditions, and the inventors have discovered the use of these compounds to provide superior, and unexpected benefits. This finding is novel. As such, by providing psilocybin and other compounds that activate the 5-$HT_{2A}$ receptor, alone or in combination with each other and/or other compounds, as pharmaceutical agents and/or dietary supplements, therapeutic and nutraceutical benefits can be realized, either individually, collectively, or in conjunction with other pharmaceutical agents and/or dietary supplements.

SUMMARY

Embodiments of the present disclosure relate to novel formulations comprising one or more of psilocybin, psilocin, baeocystin, and norpsilocin and their use in the amelioration, prevention, and/or treatment of IBS, RA, fibromyalgia, post-traumatic stress disorder (PTSD), neuropathic pain, or symptoms associated with any of the foregoing.

These and other feature, aspects, and advantages of the present embodiments will become understood with reference to the following description, appended claims, and accompanying FIGURES.

BRIEF DESCRIPTIONS OF THE DRAWINGS

FIG. 1 depicts a clinical protocol for evaluating one or more embodiments of the disclosure.

DETAILED DESCRIPTION

Some embodiments provide a composition comprising an amount of at least one alkaloid compound formulated as an alkaloid composition. The alkaloid compound can be psilocybin, psilocin, baeocystin, norpsilocin, or any combination thereof. Some embodiments can be formulated to have varying amounts of one or more alkaloid compound.

In some embodiments, an alkaloid composition can comprise an amount of a first alkaloid compound and an amount of a second alkaloid compound. In certain embodiments, an alkaloid composition comprising an amount of a first alkaloid compound and an amount of a second alkaloid compound can comprise, as the first and second alkaloid compounds, respectively, psilocybin and psilocin, psilocybin and baeocystin, psilocybin and norpsilocin, psilocin and baeocystin, psilocin and norpsilocin, or baeocystin and norpsilocin. In certain embodiments, an amount of a first alkaloid compound and an amount of a second alkaloid compound can be formulated with the amounts of the two alkaloid compounds present as a ratio. In some embodiments, a ratio of an amount of a first alkaloid compound to an amount of a second alkaloid compound can be about 1:1. In certain embodiments, a ratio of an amount of a first alkaloid compound to an amount of a second alkaloid compound can be within the range of about 10:1 to about 1:10. In this regard, a ratio of an amount of a first alkaloid compound to an amount of a second alkaloid may be about 2:1, about 3:1, about 4:1, about 5:1, about 6:1, about 7:1, about 8:1, about 9:1, about 10:1, about 1:2, about 1:3, about 1:4, about 1:5, about 1:6, about 1:7, about 1:8, about 1:9, or about 1:10, or any ratio in between.

In some embodiments, an alkaloid composition can comprise an amount of a first alkaloid compound, an amount of a second alkaloid compound, and an amount of a third alkaloid compound. In certain embodiments, an alkaloid composition comprising an amount of a first alkaloid compound, an amount of a second alkaloid compound, and an amount of a third alkaloid compound can comprise, as the first, second, and third alkaloid compounds, respectively, psilocybin, psilocin, and baeocystin, psilocybin, psilocin, and norpsilocin, psilocybin, baeocystin, and norpsilocin, or psilocin, baeocystin, and norpsilocin. In certain embodiments, an amount of a first alkaloid compound, an amount of a second alkaloid compound, and an amount of a third alkaloid compound can be formulated with the amounts of the three alkaloid compounds present as a ratio. In some embodiments, a ratio of an amount of a first alkaloid compound to an amount of a second alkaloid compound to an amount of a third alkaloid compound can be about 1:1:1. In certain embodiments, a ratio of an amount of a first alkaloid compound to an amount of a second alkaloid compound can be within the range of about 10:1:1 to about 1:10:1 to about 1:1:10. In this regard, a ratio of an amount of a first alkaloid compound to an amount of a second alkaloid to an amount of a third alkaloid compound may be about 1:1:2, 1:1:3, 1:1:4, 1:1:5, 1:1:6, 1:1:7, 1:1:8, 1:1:9, 1:1:10, 1:2:1, 1:2:2, 1:2:3, 1:2:4, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:10:9, 1:10:10, 2:1:1, 2:1:2, 2:1:3, 2:1:4, 2:1:5, 2:1:6, 2:1:7, 2:1:8, 2:1:9, 2:1:10, 2:2:1, 2:2:2, 2:2:3, 2:2:4, 2:2:5, 2:2:6, 2:2:7, 2:2:8, 2:2:9, 2:2:10, 2:3:1, 2:3:2, 2:3:3, 2:3:4, 2:3:5, 2:3:6, 2:3:7, 2:3:8, 2:3:9, 2:3:10, 2:4:1, 2:4:2, 2:4:3, 2:4:4, 2:4:5, 2:4:6, 2:4:7, 2:4:8, 2:4:9, 2:4:10, 2:5:1, 2:5:2, 2:5:3, 2:5:4, 2:5:5, 2:5:6, 2:5:7, 2:5:8, 2:5:9, 2:5:10, 2:6:1, 2:6:2, 2:6:3, 2:6:4, 2:6:5, 2:6:6, 2:6:7, 2:6:8, 2:6:9, 2:6:10, 2:7:1, 2:7:2, 2:7:3, 2:7:4, 2:7:5, 2:7:6, 2:7:7, 2:7:8, 2:7:9, 2:7:10, 2:8:1, 2:8:2, 2:8:3, 2:8:4, 2:8:5, 2:8:6, 2:8:7, 2:8:8, 2:8:9, 2:8:10, 2:9:1, 2:9:2, 2:9:3, 2:9:4, 2:9:5, 2:9:6, 2:9:7, 2:9:8, 2:9:9, 2:9:10, 2:10:1, 2:10:2, 2:10:3, 2:10:4, 2:10:5, 2:10:6, 2:10:7, 2:10:8, 2:10:9, 2:10:10, 3:1:1, 3:1:2, 3:1:3, 3:1:4, 3:1:5, 3:1:6, 3:1:7, 3:1:8, 3:1:9, 3:1:10, 3:2:1, 3:2:2, 3:2:3, 3:2:4, 3:2:5, 3:2:6, 3:2:7, 3:2:8, 3:2:9, 3:2:10, 3:3:1, 3:3:2, 3:3:3, 3:3:4, 3:3:5, 3:3:6, 3:3:7, 3:3:8, 3:3:9, 3:3:10, 3:4:1, 3:4:2, 3:4:3, 3:4:4, 3:4:5, 3:4:6, 3:4:7, 3:4:8, 3:4:9, 3:4:10, 3:5:1, 3:5:2, 3:5:3, 3:5:4, 3:5:5, 3:5:6, 3:5:7, 3:5:8, 3:5:9, 3:5:10, 3:6:1, 3:6:2, 3:6:3, 3:6:4, 3:6:5, 3:6:6, 3:6:7, 3:6:8, 3:6:9, 3:6:10, 3:7:1, 3:7:2, 3:7:3, 3:7:4, 3:7:5, 3:7:6, 3:7:7, 3:7:8, 3:7:9, 3:7:10, 3:8:1, 3:8:2, 3:8:3, 3:8:4, 3:8:5, 3:8:6, 3:8:7, 3:8:8, 3:8:9, 3:8:10, 3:9:1, 3:9:2, 3:9:3, 3:9:4, 3:9:5, 3:9:6, 3:9:7, 3:9:8, 3:9:9, 3:9:10, 3:10:1, 3:10:2, 3:10:3, 3:10:4, 3:10:5, 3:10:6, 3:10:7, 3:10:8, 3:10:9, 3:10:10, 4:1:1, 4:1:2, 4:1:3, 4:1:4, 4:1:5, 4:1:6, 4:1:7, 4:1:8, 4:1:9, 4:1:10, 4:2:1, 4:2:2, 4:2:3, 4:2:4, 4:2:5, 4:2:6, 4:2:7, 4:2:8, 4:2:9, 4:2:10, 4:3:1, 4:3:2, 4:3:3, 4:3:4, 4:3:5, 4:3:6, 4:3:7, 4:3:8, 4:3:9, 4:3:10, 4:4:1, 4:4:2, 4:4:3, 4:4:4, 4:4:5, 4:4:6, 4:4:7, 4:4:8, 4:4:9, 4:4:10, 4:5:1, 4:5:2, 4:5:3, 4:5:4, 4:5:5, 4:5:6, 4:5:7, 4:5:8, 4:5:9, 4:5:10, 4:6:1, 4:6:2, 4:6:3, 4:6:4, 4:6:5, 4:6:6, 4:6:7, 4:6:8, 4:6:9, 4:6:10, 4:7:1, 4:7:2, 4:7:3, 4:7:4, 4:7:5, 4:7:6, 4:7:7, 4:7:8, 4:7:9, 4:7:10, 4:8:1, 4:8:2, 4:8:3, 4:8:4, 4:8:5, 4:8:6, 4:8:7, 4:8:8, 4:8:9, 4:8:10, 4:9:1, 4:9:2, 4:9:3, 4:9:4, 4:9:5, 4:9:6, 4:9:7, 4:9:8, 4:9:9, 4:9:10, 4:10:1, 4:10:2, 4:10:3, 4:10:4, 4:10:5, 4:10:6, 4:10:7, 4:10:8, 4:10:9, 4:10:10, 5:1:1, 5:1:2, 5:1:3, 5:1:4, 5:1:5, 5:1:6, 5:1:7, 5:1:8, 5:1:9, 5:1:10, 5:2:1, 5:2:2, 5:2:3, 5:2:4, 5:2:5, 5:2:6, 5:2:7, 5:2:8, 5:2:9, 5:2:10, 5:3:1, 5:3:2, 5:3:3, 5:3:4, 5:3:5, 5:3:6, 5:3:7, 5:3:8, 5:3:9, 5:3:10, 5:4:1, 5:4:2, 5:4:3, 5:4:4, 5:4:5, 5:4:6, 5:4:7, 5:4:8, 5:4:9, 5:4:10, 5:5:1, 5:5:2, 5:5:3, 5:5:4, 5:5:5, 5:5:6, 5:5:7, 5:5:8, 5:5:9, 5:5:10, 5:6:1, 5:6:2, 5:6:3, 5:6:4, 5:6:5, 5:6:6, 5:6:7, 5:6:8, 5:6:9, 5:6:10, 5:7:1, 5:7:2, 5:7:3, 5:7:4, 5:7:5, 5:7:6, 5:7:7, 5:7:8, 5:7:9, 5:7:10, 5:8:1, 5:8:2, 5:8:3, 5:8:4, 5:8:5, 5:8:6, 5:8:7, 5:8:8, 5:8:9, 5:8:10, 5:9:1, 5:9:2, 5:9:3, 5:9:4, 5:9:5, 5:9:6, 5:9:7, 5:9:8, 5:9:9, 5:9:10, 5:10:1, 5:10:2, 5:10:3, 5:10:4, 5:10:5, 5:10:6, 5:10:7, 5:10:8, 5:10:9, 5:10:10, 6:1:1, 6:1:2, 6:1:3, 6:1:4, 6:1:5, 6:1:6, 6:1:7, 6:1:8, 6:1:9, 6:1:10, 6:2:1, 6:2:2, 6:2:3, 6:2:4, 6:2:5, 6:2:6, 6:2:7, 6:2:8, 6:2:9, 6:2:10, 6:3:1, 6:3:2, 6:3:3, 6:3:4, 6:3:5, 6:3:6, 6:3:7, 6:3:8, 6:3:9, 6:3:10, 6:4:1, 6:4:2, 6:4:3, 6:4:4, 6:4:5, 6:4:6, 6:4:7, 6:4:8, 6:4:9, 6:4:10, 6:5:1, 6:5:2, 6:5:3, 6:5:4, 6:5:5, 6:5:6, 6:5:7, 6:5:8, 6:5:9, 6:5:10, 6:6:1, 6:6:2, 6:6:3, 6:6:4, 6:6:5, 6:6:6, 6:6:7, 6:6:8, 6:6:9, 6:6:10, 6:7:1, 6:7:2, 6:7:3, 6:7:4, 6:7:5, 6:7:6, 6:7:7, 6:7:8, 6:7:9, 6:7:10, 6:8:1, 6:8:2, 6:8:3, 6:8:4, 6:8:5, 6:8:6, 6:8:7, 6:8:8, 6:8:9, 6:8:10, 6:9:1, 6:9:2, 6:9:3, 6:9:4, 6:9:5, 6:9:6, 6:9:7, 6:9:8, 6:9:9, 6:9:10, 6:10:1, 6:10:2, 6:10:3, 6:10:4, 6:10:5, 6:10:6, 6:10:7, 6:10:8, 6:10:9, 6:10:10, 7:1:1, 7:1:2, 7:1:3, 7:1:4, 7:1:5, 7:1:6, 7:1:7, 7:1:8, 7:1:9, 7:1:10, 7:2:1, 7:2:2, 7:2:3, 7:2:4, 7:2:5, 7:2:6, 7:2:7, 7:2:8, 7:2:9, 7:2:10, 7:3:1, 7:3:2, 7:3:3, 7:3:4, 7:3:5, 7:3:6, 7:3:7, 7:3:8, 7:3:9, 7:3:10, 7:4:1, 7:4:2, 7:4:3, 7:4:4, 7:4:5, 7:4:6, 7:4:7, 7:4:8, 7:4:9, 7:4:10, 7:5:1, 7:5:2, 7:5:3, 7:5:4, 7:5:5, 7:5:6, 7:5:7, 7:5:8, 7:5:9, 7:5:10, 7:6:1, 7:6:2, 7:6:3, 7:6:4, 7:6:5, 7:6:6, 7:6:7, 7:6:8, 7:6:9, 7:6:10, 7:7:1, 7:7:2, 7:7:3, 7:7:4, 7:7:5, 7:7:6, 7:7:7, 7:7:8, 7:7:9, 7:7:10, 7:8:1, 7:8:2, 7:8:3, 7:8:4, 7:8:5, 7:8:6, 7:8:7, 7:8:8, 7:8:9, 7:8:10, 7:9:1, 7:9:2, 7:9:3, 7:9:4, 7:9:5, 7:9:6, 7:9:7, 7:9:8, 7:9:9, 7:9:10, 7:10:1, 7:10:2, 7:10:3, 7:10:4, 7:10:5, 7:10:6, 7:10:7, 7:10:8, 7:10:9, 7:10:10, 8:1:1, 8:1:2, 8:1:3, 8:1:4, 8:1:5, 8:1:6, 8:1:7, 8:1:8, 8:1:9, 8:1:10, 8:2:1, 8:2:2, 8:2:3, 8:2:4, 8:2:5, 8:2:6, 8:2:7, 8:2:8, 8:2:9, 8:2:10, 8:3:1, 8:3:2, 8:3:3, 8:3:4, 8:3:5, 8:3:6, 8:3:7, 8:3:8, 8:3:9, 8:3:10, 8:4:1, 8:4:2, 8:4:3, 8:4:4, 8:4:5, 8:4:6, 8:4:7, 8:4:8, 8:4:9, 8:4:10, 8:5:1, 8:5:2, 8:5:3, 8:5:4, 8:5:5, 8:5:6, 8:5:7, 8:5:8, 8:5:9, 8:5:10, 8:6:1, 8:6:2, 8:6:3, 8:6:4, 8:6:5, 8:6:6, 8:6:7, 8:6:8, 8:6:9, 8:6:10, 8:7:1, 8:7:2, 8:7:3, 8:7:4, 8:7:5, 8:7:6, 8:7:7, 8:7:8, 8:7:9, 8:7:10, 8:8:1, 8:8:2, 8:8:3, 8:8:4, 8:8:5, 8:8:6, 8:8:7, 8:8:8, 8:8:9, 8:8:10, 8:9:1, 8:9:2, 8:9:3, 8:9:4, 8:9:5, 8:9:6, 8:9:7, 8:9:8, 8:9:9, 8:9:10, 8:10:1, 8:10:2, 8:10:3, 8:10:4, 8:10:5, 8:10:6, 8:10:7, 8:10:8, 8:10:9, 8:10:10, 9:1:1, 9:1:2, 9:1:3, 9:1:4, 9:1:5, 9:1:6, 9:1:7, 9:1:8, 9:1:9, 9:1:10, 9:2:1, 9:2:2, 9:2:3, 9:2:4, 9:2:5, 9:2:6, 9:2:7, 9:2:8, 9:2:9, 9:2:10, 9:3:1, 9:3:2, 9:3:3, 9:3:4, 9:3:5, 9:3:6, 9:3:7, 9:3:8, 9:3:9, 9:3:10, 9:4:1, 9:4:2, 9:4:3, 9:4:4, 9:4:5, 9:4:6, 9:4:7, 9:4:8, 9:4:9, 9:4:10, 9:5:1, 9:5:2, 9:5:3, 9:5:4, 9:5:5, 9:5:6, 9:5:7, 9:5:8, 9:5:9, 9:5:10, 9:6:1, 9:6:2, 9:6:3, 9:6:4, 9:6:5, 9:6:6, 9:6:7, 9:6:8, 9:6:9, 9:6:10, 9:7:1, 9:7:2, 9:7:3, 9:7:4, 9:7:5, 9:7:6, 9:7:7, 9:7:8, 9:7:9, 9:7:10, 9:8:1, 9:8:2, 9:8:3, 9:8:4, 9:8:5, 9:8:6, 9:8:7, 9:8:8, 9:8:9, 9:8:10, 9:9:1, 9:9:2, 9:9:3, 9:9:4, 9:9:5, 9:9:6, 9:9:7, 9:9:8, 9:9:9, 9:9:10, 9:10:1, 9:10:2, 9:10:3, 9:10:4, 9:10:5, 9:10:6, 9:10:7, 9:10:8, 9:10:9, 9:10:10, 10:1:1, 10:1:2, 10:1:3, 10:1:4, 10:1:5, 10:1:6, 10:1:7, 10:1:8, 10:1:9, 10:1:10, 10:2:1, 10:2:2, 10:2:3, 10:2:4, 10:2:5, 10:2:6, 10:2:7, 10:2:8, 10:2:9, 10:2:10, 10:3:1, 10:3:2, 10:3:3, 10:3:4, 10:3:5, 10:3:6, 10:3:7, 10:3:8, 10:3:9, 10:3:10, 10:4:1, 10:4:2, 10:4:3, 10:4:4, 10:4:5, 10:4:6, 10:4:7, 10:4:8, 10:4:9, 10:4:10, 10:5:1, 10:5:2, 10:5:3, 10:5:4, 10:5:5, 10:5:6, 10:5:7, 10:5:8, 10:5:9, 10:5:10, 10:6:1, 10:6:2, 10:6:3, 10:6:4, 10:6:5, 10:6:6, 10:6:7, 10:6:8, 10:6:9, 10:6:10, 10:7:1, 10:7:2, 10:7:3, 10:7:4, 10:7:5, 10:7:6, 10:7:7, 10:7:8, 10:7:9, 10:7:10, 10:8:1, 10:8:2, 10:8:3, 10:8:4, 10:8:5, 10:8:6, 10:8:7, 10:8:8, 10:8:9, 10:8:10, 10:9:1, 10:9:2, 10:9:3, 10:9:4, 10:9:5, 10:9:6, 10:9:7, 10:9:8, 10:9:9, 10:9:10, 10:10:1, 10:10:2, 10:10:3, 10:10:4, 10:10:5, 10:10:6, 10:10:7, 10:10:8, 10:10:9, 10:10:10, or any ratio in between.

In some embodiments, an alkaloid composition can comprise an amount of psilocybin, an amount of psilocin, an amount of baeocystin, and an amount of norpsilocin. In certain embodiments, an amount of psilocybin, an amount of psilocin, an amount of baeocystin, and an amount of norpsilocin can be formulated with the amounts of the four alkaloid compounds present as a ratio. The ratio can be understood as comprising a "part" of psilocybin, psilocin, baeocystin, or norpsilocin. For example, an alkaloid composition may comprise a ratio of 4:1:10:6, psilocybin to psilocin to baeocystin to norpsilocin, corresponding to 4 parts psilocybin, 1 part psilocin, 10 parts baeocystin, and 6 parts norpsilocin. The individual amount of psilocybin, psilocin, baeocystin, or norpsilocin may be as low as 1 part, may be as high as 10 parts, or may be any value therebetween.

In some embodiments, an alkaloid composition comprising an amount of at least one alkaloid compound may be formulated such that the amount of the at least one alkaloid compound is a micro-dose. The term "micro-dose" refers to an amount of the at least one alkaloid compound being less than 5 mg. In some embodiments a micro-dose may constitute about 10 μg to about 1 mg. For example, a micro-dose can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, or any range or amount in between any two of the preceding values and any other ranges or amounts disclosed herein. In other instances, a micro-dose can be about 1 mg to about 5 mg. For example, a micro-dose can be about 1 mg, about 2 mg, about 3 mg, about 4 mg, about 5 mg, or any range or amount in between any two of the preceding values and any other ranges or amounts disclosed herein. The scope and meaning of micro-dose which will be clear to the skilled artisan based upon the context in which these terms are used.

In some embodiments, an alkaloid composition comprising an amount of at least one alkaloid compound may be formulated such that the amount of the at least one alkaloid compound is a macro-dose. The term "macro-dose" refers to an amount of the at least one alkaloid compound being about 5 mg to about 50 mg. For example, a macro-dose can be about 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, or any range or amount in between any two of the preceding values and any other ranges or amounts disclosed herein.

In certain embodiments, an alkaloid composition, as described herein, may further comprise an amount of one or more cannabinoids. The one or more cannabinoids is not particularly limited. In some embodiments, the one or more cannabinoids may comprise at least one of endocannabinoids (produced naturally in the body by animals), phytocannabinoids (found in *cannabis* and some other plants), synthetic cannabinoids (may be manufactured artificially), and any ligand that can act on a cannabinoid receptor. Exemplary cannabinoids include, but are not limited to cannabidiol (CBD), cannabinol (CBN), tetrahydrocannabinol (THC), cannabigerol (CBG), delta(9)-tetrahydrocannabinolic acid, cannabidiolic acid. Other cannabinoids not explicitly listed would readily be envisaged by those of skill in the art, in view of the disclosure contained herein.

In some embodiments, an amount of one or more cannabinoids, as disclosed herein, can be about 10 μg to about 10 g. For example, the amount of the one or more cannabinoids in the composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 2 g, 3 g, 4 g, 5 g, 6 g, 7 g, 8 g, 9 g, 10 g, or any range or amount in between any two of the preceding values and any other ranges or amounts disclosed herein.

In some embodiments, an alkaloid composition, as described herein, may further comprise an amount of one or more of erinacines, hericenones, cyanthane terpenes, or extracts from *Hericium* mushroom species. Exemplary examples of erinacines include Erinacines A-K, Erinacine P and Erinacine Q. Exemplary examples of hericenones are Hericenones A-K. Other erinacines and hericenones not explicitly listed would readily be envisaged by those of skill in the art, in view of the disclosure contained herein.

In some embodiments, an amount of one or more of erinacines, hericenones, cyanthane terpenes, or extracts from *Hericium* mushroom species, such as Hericine A, as disclosed herein, can be about 5 mg to about 10 g. For example, the amount of the one or more of erinacines, hericenones, cyanthane terpenes, or extracts from *Hericium* mushroom species in the composition can be about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 2 g, 3 g, 4 g, 5 g, 6 g, 7 g, 8 g, 9 g, 10 g, or any range or amount in between any two of the preceding values and any other ranges or amounts disclosed herein.

In certain embodiments, an alkaloid composition, as described herein, may further comprise an amount of at least one vitamin. Non-exhaustive examples of vitamins include retinol (vitamin A), thiamine (vitamin B1), riboflavin (vitamin B2), niacin (vitamin B3), pantothenic acid (vitamin B5), pyridoxine, pyridoxamine, or pyridoxal (vitamin B6), biotin (vitamin B7) or pharmaceutically acceptable salts thereof, folic acid (vitamin B9) or pharmaceutically acceptable salts thereof, cobalamin (vitamin B12), choline, ascorbic acid (vitamin C) or pharmaceutically acceptable salts thereof, ergocalciferol (vitamin D2), calciferol (vitamin D3), 22-dihydroergocalciferol (vitamin D4), sitocalciferol (vitamin D5), tocopherol (vitamin E), phylloquinone (vitamin K1), menaquinone (vitamin K2), menadione (vitamin K3), or any combination of the foregoing. Other vitamins not explicitly listed would readily be envisaged by those of skill in the art, in view of the disclosure contained herein.

In some embodiments, an amount of least one vitamin, as disclosed herein, can be about 10 μg to about 10 g. For example, the amount of the at least one vitamin in the composition can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 575

μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 5 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 2 g, 3 g, 4 g, 5 g, 6 g, 7 g, 8 g, 9 g, 10 g, or any range or amount in between any two of the preceding values and any other ranges or amounts disclosed herein.

In some embodiments, an alkaloid composition, as described herein, may further comprise an amount of one or more psychobiotics. In certain embodiments, the one or more psychobiotics may be selected from the group consisting of *Lactobacillus helveticus, Lactobacillus helveticus* NSB, *Bifidobacterium longum, Lactobacillus casei, Lactobacillus plantarum, Lactobacillus plantarum* PS128, *Lactobacillus acidophilus, Lactobacillus delbrueckii* subsp. *bulgaricus, Bifidobacterium breve, Bifidobacterium infantis, Streptococcus salivarius, Lactobacillus rhamnosus, Bifidobacterium bifidum, Bifidobacterium bifidum* R007, *Lactobacillus rhamnosus* JB-1, *Lactobacillus* gasseri, and any combination of thereof. Other psychobiotics not explicitly listed would readily be envisaged by those of skill in the art, in view of the disclosure contained herein.

In some embodiments, an amount of one or more psychobiotics, as disclosed herein, can be about 5 mg to about 10 g. For example, the amount of one or more psychobiotics in the composition can be about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 2 g, 3 g, 4 g, 5 g, 6 g, 7 g, 8 g, 9 g, 10 g, or any range or amount in between any two of the preceding values and any other ranges or amounts disclosed herein.

In some embodiments, an alkaloid composition, as described herein, may further comprise an amount of one or more prebiotics. Non-exhaustive examples of prebiotics include sorbitol and alginate. Other prebiotics not explicitly listed would readily be envisaged by those of skill in the art, in view of the disclosure contained herein.

In some embodiments, an amount of one or more prebiotics, as disclosed herein, can be about 5 mg to about 10 g. For example, the amount of one or more prebiotics in the composition can be about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 2 g, 3 g, 4 g, 5 g, 6 g, 7 g, 8 g, 9 g, 10 g, or any range or amount in between any two of the preceding values and any other ranges or amounts disclosed herein.

In some embodiments, an alkaloid composition, as described herein, may further comprise an amount of docosahexaenoic acid (DHA). In certain embodiments, DHA may be present due to algal oil. Other forms of DHA or DHA-containing materials not explicitly listed would readily be envisaged by those of skill in the art, in view of the disclosure contained herein.

In some embodiments, an amount of DHA, as disclosed herein, can be about 5 mg to about 10 g. For example, the amount of DHA in the composition can be about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 2 g, 3 g, 4 g, 5 g, 6 g, 7 g, 8 g, 9 g, 10 g, or any range or amount in between any two of the preceding values and any other ranges or amounts disclosed herein.

In some embodiments, an alkaloid composition, as described herein, may further comprise an amount of at least one medicinal mushroom. In certain embodiments, the at least one medicinal mushroom may be selected from the group consisting of a species having the *Antrodia* genus, a species having the *Beauveria* genus, a species having the *Copelandia* genus, a species having the *Cordyceps* genus, a species having the *Ganoderma* genus, a species having the Grifola genus, a species having the *Inonotus* genus, a species having the *Isaria* genus, a species having the *Panaeolus* genus, a species having the *Phellinus* genus, and any combination of thereof. Other medicinal mushrooms not explicitly listed would readily be envisaged by those of skill in the art, in view of the disclosure contained herein.

In some embodiments, an amount of at least one medicinal mushroom, as disclosed herein, can be about 5 mg to about 10 g. For example, the amount of at least one medicinal mushroom in the composition can be about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 2 g, 3 g, 4 g, 5 g, 6 g, 7 g, 8 g, 9 g, 10 g, or any range or amount in between any two of the preceding values and any other ranges or amounts disclosed herein.

In some embodiments, an alkaloid composition, as described herein, may further comprise an amount of at least one excipient. The excipients are not particularly limited. Exemplary excipients include, but are not limited to: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (castor oil, diacetylated monoglycerides, diethyl phthalate, glycerol, mono- and di-acetylated monoglycerides, propylene glycol, triacetin, triethyl citrate); polymers (cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or thickening agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin (Bloom strength 50-100), guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); surfactants (simethicone); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); vehicle: solid carrier (sugar spheres); vehicle: sterile (Bacteriostatic water for injection, bacteriostatic sodium chloride injection); water repelling agents (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20 cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in alkaloid compositions, as described herein.

In some embodiments, an alkaloid composition, as described herein, may be formulated to be administered via an oral route. In certain embodiments, as alkaloid composition formulated to be administered via an oral route may be in the form of a powder, a granule, a suspension, an aqueous solution, an oil-based solution, a capsule (soft, hard, gel, or plant-based), a pill, a tablet, a caplet, a sachet, a gum, or a dissolvable oral strip. In the aforementioned oral formulations, the formulation may comprise one or more of the aforementioned excipients. One skilled in the art would recognize the excipients appropriate for the particular oral delivery system contemplated. In addition, various methods of time release and location specific release are contemplated, including immediate release, delayed release, and sustained release.

In certain embodiments, an alkaloid composition, as described herein, may be formulated as a dietary supplement, a nutritional supplement, or a pharmaceutical composition.

In some embodiments, an alkaloid composition, as described herein, can be administered to treat, prevent, or ameliorate a variety of diseases selected from the group consisting of neurological disorders and neurological diseases such as neuropathic pain, chronic pain, migraine, PTSD, pruritus, RA, sleep apnea, Huntington's disease, Alzheimer's disease, Parkinson's disease, amyotrophic lateral sclerosis (ALS), hypertension, incontinence, diabetes, hepatitis C, multiple sclerosis (MS), osteoporosis, dystonia, HIV, epilepsy, fibromyalgia, Tourette syndrome, gastrointestinal such as IBS, Crohn's disease, ulcerative colitis, symptoms associated with any of the foregoing, and any combination thereof. In preferable embodiments, an alkaloid composition, as described herein, can be administered to treat, prevent, or ameliorate a disease selected from the group consisting of RA, fibromyalgia, IBS, PTSD, neuropathic pain, symptoms associated with any of the foregoing, and combination thereof.

In certain embodiments, administering an alkaloid composition to treat, prevent, or ameliorate a disease, as described herein, can comprise using a micro-dosing regimen. A micro-dosing regimen may comprise the administration of an alkaloid composition comprising a micro-dose, one or more times during a 24-hour period over a number of days. For instance, a micro-dosing regimen may comprise administering an alkaloid composition comprising a micro-dose once per day for one or more days, weeks, or months. The length of time of administration and number of doses is not particularly limited and one of skill in the art would understand how to manipulate the dosage regimen to treat a particular disorder or disease in view of the instant disclosure. A micro-dosing regimen may comprise the administration an alkaloid composition comprising a micro-dose every day, every other day, two times per week. A micro-dosing regimen can also be alternating sequential periods of administration days followed by days with no administration of doses described herein. For example, such a regimen may comprise the administration of an alkaloid composition comprising a micro-dose once per day for three days, followed by three days of no administration. This cycle may also be repeated.

In some embodiments, administering an alkaloid composition to treat, prevent, or ameliorate a disease, as described herein, can comprise using a macro-dosing regimen. A macro-dosing regimen may comprise the administration of an alkaloid composition comprising a macro-dose once. In certain embodiments, a macro-dosing regimen may comprise the administration of an alkaloid composition comprising a macro-dose more than once, wherein the administration is spread over an interval. For example, and without limitation, a macro-dosing regimen may comprise the administration of an alkaloid composition comprising a macro-dose once a week, once every several weeks, or once every several months. The length of time of administration and number of doses is not particularly limited and one of skill in the art would understand how to manipulate the dosage regimen to treat a particular disorder or disease in view of the instant disclosure.

Certain embodiments for administering an alkaloid composition to treat, prevent, or ameliorate a disease, as described herein, may mix and/or combine micro-dosing and macro-dosing regimens.

In certain embodiments, the subject is a human. In some embodiments, the subject is an animal. An animal may be, for example and without limitation, a horse, a dog, a cat, a mouse, or a rabbit, or other mammal. The age of the human is not particularly limited.

Without being bound by a particular theory, it is believed that the one or vitamins may activate nerve endings, and enhances the neurogenic effects of psilocybin, psilocin, erinacines and hericenones by helping these nootropics cross the blood brain barrier, and migrate throughout the nervous systems, and to its end points, thereby providing unexpectedly superior results. Moreover, vitamins, as disclosed herein, may act as a vasodilator, thereby improving blood flow in the brain by relaxing constricted blood vessels. This unique combination not only rebuilds myelin upon the axons, but it also activates new astrocyte and/or astroglia cells, and neuronal nodes of crossings such as the synaptic regions, particularly in the hippocampus.

Methods of treatment of instant invention include utilizing the disclosed compositions to treat RA. Without being bound to any particular theory, the proposed mechanism of action is based on 5-$HT_{2A}$ receptor activation. The inventors understand the correlation between mutations in the gene that encodes for the 5-$HT_{2A}$ receptor with RA, suggesting dysfunction in signalling. 5-$HT_{2A}$ receptor agonists have been shown to reduce pain in RA. Pain indications require repeat dosing to maintain an effective level of the compound in the body. Inducing hallucinations may be a significant drawback of psychedelics for indications outside of those employing psychotherapy. Therefore, a micro-dose and/or macro-dose approach, as disclosed herein, may be the preferred regimen for development of an alkaloid composition-based therapy in treatment of RA. Nevertheless, RA subjects also experience a significant amount of depression due to their condition. Thus, certain embodiments may comprise a micro-dosing and macro-dosing regimen to treat both RA and associated psychotherapy to treat depression, anxiety, PTSD, and the like.

Without being bound by any particular theory, fibromyalgia is linked to polymorphism or genetic mutations in the gene for the 5-$HT_{2A}$ receptor. The inventors understand this correlation along with the ability of compositions of the instant invention to act as 5-$HT_{2A}$ receptor agonists. As a result, certain embodiments of the instant invention can comprise micro-dosing and/or macro-dosing regimens as set forth herein to be used in the treatment of fibromyalgia. In some embodiments, alkaloid compositions as set forth herein can be used to treat fibromyalgia. In some embodiments, a dosing regimen for treating fibromyalgia could comprise both a micro-dosing portion and a macro-dosing portion. In some embodiments where both macro-dosing and micro-dosing is employed, the regimen may comprise one or more macro-doses followed by one or more micro-doses.

Without being bound by any particular theory, it is believed that irritable bowel syndrome (IBS) has also been correlated with mutations in the gene for 5-$HT_{2A}$ receptors. The treatment methods contemplated herein include a method of treating IBS by administering the disclosed compositions. The 5-$HT_{2A}$ receptors are involved in the motility of the intestines and in visceral pain. There is currently no effective treatment for IBS but many of the ingredients suggested for the micro-dose regimen can have a positive effect on serotonin and GABA signalling dysfunction, depression associated with the condition, inflammation, pain, and sleep. The micro-dose regimen disclosed herein can be utilized to address many elements of this condition including neuropathic pain, inflammation, depression, and sleep.

Without being bound by any particular theory, it is believed that there may be central nervous system (CNS) components to the indications of RA, IBS and fibromyalgia, the action of the proposed formulation would primarily be manifested in the periphery. For this reason, certain embodiments that substitute psilocybin for another 5-$HT_{2A}$ agonist derived from mushrooms (baeocystin or norpsilocin) may be preferable if they may not cross the blood brain barrier and therefore may not have psychogenic activity (e.g., inducing hallucinations).

The term "pharmaceutically acceptable salts" includes salts of the active compounds which are prepared with relatively nontoxic acids or bases, depending on the particular substituents found on the compounds described herein. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids, and the like (see, for example, Berge et al., Journal of Pharmaceutical Science, 66: 1-19 (1977), which is hereby incorporated by reference in its entirety). Certain specific compounds of the present application contain both basic and acidic functionalities that allow the compounds to be converted into either base or acid addition salts.

The term "pharmaceutical," "pharmaceutical composition" or "pharmaceutical formulation" encompasses "neutraceutical" (also referred to as "nutraceutical"), "neutraceutical composition" or "neutraceutical formulation", respectively. "Neutraceutical formulations" or "neutraceutical compositions" may include a pharmaceutically acceptable carrier, such as those described herein.

As used herein, the terms "preventing," "treating," "treatment," "ameliorating," and the like are used herein to generally refer to obtaining a desired pharmacological and physiological effect and can also refer to a nutritional or nutraceutical effect, the scopes and meanings of which will be clear to the skilled artisan based upon the context in which these terms are used. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms, conditions, and co-morbidities.

The terms "dietary supplement," or "nutritional supplement" have the meaning ascribed to them under the Federal Food, Drug & Cosmetic Act.

As used herein, a "prebiotic" refers a compound that can be used as food by a probiotic or psychobiotic organism. A "prebiotic" would also be understood by those skilled in the art to be a compound that surpresses harmful endemic bacterial populations.

As used herein, the term "excipient" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release of a tablet or caplet from equipment in which it is formed, and so forth.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

In addition, the appropriate dosage of the compositions can depend, for example, on the condition to be treated, the severity and course of the condition, whether the composition is administered for preventive or therapeutic purposes, previous therapy, the patient's clinical history and response to the composition, the type of composition used, and the discretion of the attending physician. The composition can be suitably administered to the patient at one time or over a series of treatments and may be administered to the patient at any time from diagnosis onwards. The composition may be administered as the sole treatment or in conjunction with other drugs or therapies useful in treating the condition in question.

While exemplary embodiments, aspects and variations have been provided herein, those of skill in the art will recognize certain modifications, permutations, additions and combinations and certain sub-combinations of the embodiments, aspects, and variations. It is intended that the following claims are interpreted to include all such modifications, permutations, additions and combinations and certain sub-combinations of the embodiments, aspects and variations are within their scope.

EXAMPLES

Example 1

A rodent study will be conducted using a widely accepted model of PTSD; examples include a social defeat model, a single-prolonged stress model, an unpredictable variable stress model, or an inescapable foot-shock model.

Five treatment groups will be tested in the study: (i) no treatment, (ii) a micro-dose psilocybin alone (human equivalent of 1.5 mg, dosed every other day p.o.), (iii) a micro-dose according to an embodiment, as disclosed herein (containing human equivalent of 1.5 mg, dosed every other day p.o.), (iv) a macro-dose according to an embodiment, as disclosed herein (human equivalent of 5 mg, dosed every other day p.o.), and (v) a positive control (sertraline human equivalent of 50 mg, dosed daily p.o.).

The rodent model of PTSD will be induced by presenting the animals with a traumatic experience or several traumatic experiences, as required by the model. The animals will be verified as expressing PTSD-induced changes in behavior prior to dosing. The treatments described above will then be applied for 30 days and the animals will be observed for PTSD behaviors including fear-related memory and anxietylike behavior, arousal, depression, sleep disturbance, as well as markers of hypothalamus-pituitary-adrenal axis function, and inflammation.

This study will provide a preliminary assessment of the effects of one or more embodiments, as disclosed herein, compared to no treatment as well as an accepted standard treatment for PTSD, and will document any synergistic effects that may be present as compared to psilocybin alone.

Example 2

A rodent study will be conducted using a widely accepted model of RA; examples include a collagen antibody induced arthritis, or a transgenic mouse model.

Five treatment groups will be tested in the study: (i) no treatment, (ii) a micro-dose psilocybin alone (human equivalent of 1.5 mg, dosed every other day p.o.), (iii) a micro-dose according to an embodiment, as disclosed herein (containing human equivalent of 1.5 mg, dosed every other day p.o.), (iv) a macro-dose according to an embodiment, as disclosed herein (human equivalent of 5 mg, dosed every other day p.o.), and (v) a positive control (corticosteroid).

RA symptoms will be induced using one or more of the models mentioned above and verified as effective prior to initiation of dosing. Animals will then be treated for 30 days with one of the five treatments. Animals pain threshold, clinical arthritic score, and proinflammatory cytokines will be repeatedly tested over the 30 days.

This study will provide a preliminary assessment of the effects of one or more embodiments, as disclosed herein, compared to no treatment as well as an accepted standard treatment for RA, and will document any synergistic effects that may be present as compared to psilocybin alone.

Example 3

A rodent study will be conducted using a widely accepted models of IBS; examples include either a colorectal distension (with balloon) model using high anxiety animals, stress induced hypermotility and visceral pain model, or a model inducing visceral pain or sensitivity by rectal injection of mustard oil, capsaicin, or acetic acid.

Five treatment groups will be tested in the study: (i) no treatment, (ii) a micro-dose psilocybin alone (human equivalent of 1.5 mg, dosed every other day p.o.), (iii) a micro-dose according to an embodiment, as disclosed herein (containing human equivalent of 1.5 mg, dosed every other day p.o.), (iv) a macro-dose according to an embodiment, as disclosed herein (human equivalent of 5 mg, dosed every other day p.o.), and (v) a positive control (tegaserod or fexofenadine will be used as a positive control depending upon the model used).

Sequalae resembling IBS (inflammation and visceral hypersensitivity) will be induced using one or more of the models mentioned above and verified as effective prior to initiation of dosing. Animals will then be treated for 30 days with one of the four treatments. Animals will be monitored for visceral hypersensitivity by a trained observer who will count abdominal muscle contractions when a colonic balloon catheter is inserted. Inflammation will be assessed post-mortem in animals sacrificed throughout the study.

This study will provide a preliminary assessment of the effects of one or more embodiments, as disclosed herein, compared to no treatment and an established pharmaceutical treatment as well as any synergistic effects that may be present as compared to psilocybin alone.

Example 4

A rodent study will be conducted using a widely accepted model of fibromyalgia; examples include repeated muscular trauma, depletion of biogenic amines, and stress.

Five treatment groups will be tested in the study: (i) no treatment, (ii) a micro-dose psilocybin alone (human equivalent of 1.5 mg, dosed every other day p.o.), (iii) a micro-dose according to an embodiment, as disclosed herein (containing human equivalent of 1.5 mg, dosed every other day p.o.), (iv) a macro-dose according to an embodiment, as disclosed herein (human equivalent of 5 mg, dosed every other day p.o.), and (v) a positive control (gabapentin or a SSRI).

Pain symptoms will be induced using injection of reserpine and verified as effective prior to initiation of dosing. Animals will then be treated for 30 days with one of the five treatments. Animals pain threshold (hyperalgesia), rat grimace scale, and depressive behavior will be repeatedly tested over the 30 days.

This study will provide a preliminary assessment of the effects of one or more embodiments, as disclosed herein, compared to no treatment as well as an accepted standard treatment for fibromyalgia, and will document any synergistic effects that may be present as compared to psilocybin alone.

Example 5

The following discussion includes the details of a clinical study that will further elucidate the features of the instant invention, as depicted in FIG. 1. The objective of this study is to investigate the safety and efficacy of a micro-dose according to an embodiment alone and in combination with psychotherapy, compared to placebo, for symptoms of PTSD.

Primary Outcome:

The protocol will look for a change from Baseline in the Clinical Administered PTSD Scale (CAPS-IV) total score derived by an independent rater from Baseline to Post-treatment (9, 13- and 21-weeks post-baseline) of a micro-dose according to an embodiment compared to placebo.

Secondary Outcomes:

The protocol will also look for:

- Change from Baseline in the Clinical Administered PTSD Scale (CAPS-IV) total score derived by an independent rater from Baseline to Post-treatment (13 and 21-weeks post-baseline) of a micro-dose according to an embodiment compared to placebo.
- Change from Baseline in the Clinical Global Improvement Scale (CGI) derived by an independent rater from Baseline to Post-treatment (9, 13 and 21-weeks post-baseline) of a micro-dose according to an embodiment compared to placebo.
- Changes from Baseline in self-reported symptoms of PTSD as assessed by the Post-Traumatic Diagnostic Scale (PCL-5) (9, 13- and 21-weeks post-baseline) of a micro-dose according to an embodiment compared to placebo.
- Changes from Baseline in self-reported functional impairment as assessed by the Sheehan Disability Scale (SDS) score (9, 13- and 21-weeks post-baseline) of a micro-dose according to an embodiment compared to placebo.
- Changes from Baseline in quality of life as assessed by the WHOQOL-BREF score (9, 13- and 21-weeks post-baseline) of a micro-dose according to an embodiment compared to placebo.

Changes from Baseline in Drug Effect Questionnaire scores of a micro-dose according to an embodiment compared to placebo throughout the treatment period (weeks 1-8).

Safety Outcomes:

To confirm the safety of the disclosed treatment methods, the protocol will evaluate:

- Incidence of adverse events, spontaneously reported adverse events (adverse reactions) and serious adverse events in participants receiving psilocybin compared to active placebo
- Incidence of clinically relevant abnormal blood pressure (BP), heart rate (HR) and temperature
- Incidence of clinically relevant abnormal clinical chemistry and hematology parameters Suicidality as assessed with the Columbia Suicide Severity Rating Scale Study Design This study is a proof-of-concept study that will assess the safety and preliminary efficacy of a micro-dose according to an embodiment as a treatment for PTSD. The planned sample size for this study is 20 participants.

| Study Arm | Number of Participants |
|---|---|
| Combination Micro-dose Product | N = 5 |
| Combination Micro-dose Product + Trauma-focused Psychotherapy | N = 5 |
| Placebo | N = 5 |
| Placebo + Trauma-focused Psychotherapy | N = 5 |
| Total | N = 20 |

Schedule of Assessments

| Procedures/ assessments | Visit 1 Screening −6 to −1 weeks | V2 Baseline | V3 Check-in Call Weeks 1-8 post V2 | V4 Outcome Assessment Week 9 | V5 Outcome Assessment Week 13 | V6 Outcome Assessment Week 21 |
|---|---|---|---|---|---|---|
| Informed consent | X | | | | | |
| Eligibility assessment | X | X | | | | |
| Medical/ psychiatric history | X | | | | | |
| Collect concomitant medications | X | X | X | X | X | X |
| Physical examination and Brief neurological exam | X | | | | | |
| Structured Interview for Diagnosis | X | | | | | |
| Urine drugs of abuse screen | X | X | X | | X | |
| Urine pregnancy test | X | | X | | X | |
| Clinical safety blood panel, and HIV* | X | | | X | X | X |
| CAPS-5, CGI, PCL-5, BDI-II, SDS, WHOQOL-BREF | | X | | X | X | X |
| Study enrollment | | X | | | | |
| Weekly TF-CBT session (for psychotherapy arms) | | | X | | | |
| Dispense IP | | | X | | | |
| Return IP | | | | X | | |
| Study Diary | | X** | X** | | | |
| General well-being check | | X | X | X | X | X |
| Vitals: heart rate, blood pressure, temperature | | | | | X | |
| DEQ | | X | X | X | X | X |
| C-SSRS | X | X | X | X | X | X |
| RPQ | | | | | | X |
| Collect Adverse events | | X | X | X | X | X |

Abbreviations

| | | | |
|---|---|---|---|
| CAPS | Clinician Administered PTSD Scale | C-SSRS | Columbia Suicide Severity Rating Scale |
| CGI | Clinical Global Improvement Scale | SDS | Sheehan Disability Scale |
| BDI-II | Beck Depression Inventory II | DEQ | Drug Effects Questionnaire |
| PCL-5 | Post-Traumatic Diagnostic Scale | RPQ | Research Participation Questionnaire |
| IP | Investigational Product | TF-CBT | Trauma-Focused Cognitive Behavioral Therapy |

While a number of exemplary embodiments, aspects and variations have been provided herein, those of skill in the art will recognize certain modifications, permutations, additions and combinations and certain sub-combinations of the embodiments, aspects, and variations. It is intended that the following claims are interpreted to include all such modifications, permutations, additions and combinations and certain sub-combinations of the embodiments, aspects and variations are within their scope.

The invention claimed is:

1. An alkaloid composition comprising a first alkaloid compound selected from the group consisting of psilocybin and psilocin and a second alkaloid compound selected from the group consisting of baeocystin and norpsilocin, wherein an amount of the first alkaloid compound and an amount of the second alkaloid compound are present in a ratio ranging from about 1:3 to about 1:10 by weight, wherein the alkaloid composition is formulated as an oral formulation, wherein the oral formulation is in a form of a granule, a capsule, a pill, a caplet, a sachet, a gum, or a dissolvable oral strip.

2. The alkaloid composition of claim 1, wherein the first alkaloid compound is psilocybin.

3. The alkaloid composition of claim 2, wherein the second alkaloid compound is baeocystin.

4. The alkaloid composition of claim 2, wherein the second alkaloid is norpsilocin.

5. The alkaloid composition of claim 1, further comprising cannabidiol.

6. The alkaloid composition of claim 1, wherein the alkaloid composition further comprises one selected from the group consisting of an erinacines, hericenones, cyanthane terpenes, extracts from *Hericium* mushroom, and any combination thereof.

7. The alkaloid composition of claim 1, further comprising a psychobiotic.

8. The alkaloid composition of claim 7, wherein the psychobiotic is *Lactobacillus rhamnosus*.

9. The alkaloid composition of claim 1, further comprising a prebiotic.

10. The alkaloid composition of claim 1, further comprising one or more medicinal mushrooms or extracts thereof.

11. The alkaloid composition of claim 1, further comprising docosahexaenoic acid.

* * * * *